United States Patent
Kuhns

(10) Patent No.: US 11,771,617 B2
(45) Date of Patent: Oct. 3, 2023

(54) LIGHT THERAPY SYSTEM

(71) Applicant: HYPERICE IP SUBCO, LLC, Irvine, CA (US)

(72) Inventor: Hampden D. Kuhns, Reno, NV (US)

(73) Assignee: Hyper Ice, Inc., Irvine, CA (US)

( * ) Notice: Subject to any disclaimer, the term of this patent is extended or adjusted under 35 U.S.C. 154(b) by 401 days.

(21) Appl. No.: 16/785,200

(22) Filed: Feb. 7, 2020

(65) Prior Publication Data

US 2020/0253813 A1     Aug. 13, 2020

Related U.S. Application Data

(60) Provisional application No. 62/802,686, filed on Feb. 7, 2019.

(51) Int. Cl.
| | | |
|---|---|---|
| *A61H 9/00* | (2006.01) | |
| *A61N 5/06* | (2006.01) | |
| *A61N 5/067* | (2006.01) | |

(52) U.S. Cl.
CPC ......... *A61H 9/0092* (2013.01); *A61N 5/0622* (2013.01); *A61H 2201/10* (2013.01); *A61H 2201/164* (2013.01); *A61H 2201/5071* (2013.01); *A61H 2201/5092* (2013.01); *A61H 2203/0431* (2013.01); *A61N 5/067* (2021.08);
(Continued)

(58) Field of Classification Search
CPC .............. A61H 9/0092; A61H 2201/10; A61H 2201/5092; A61H 2209/00; A61H 2203/0431; A61N 5/0622
See application file for complete search history.

(56) References Cited

U.S. PATENT DOCUMENTS

| 6,443,978 B1 | 9/2002 | Zharov |
|---|---|---|
| 10,518,102 B2 † | 12/2019 | Kaandorp |
| 2007/0129776 A1 † | 6/2007 | Robins |

(Continued)

FOREIGN PATENT DOCUMENTS

| WO | 2018026680 | † | 2/2018 |
|---|---|---|---|
| WO | 2019162935 | † | 8/2019 |

OTHER PUBLICATIONS

International Search Report and Written Opinion of PCT/US2020/017286 dated May 6, 2020, 14 pages.

*Primary Examiner* — Timothy A Stanis
(74) *Attorney, Agent, or Firm* — Goodwin Procter LLP

(57) ABSTRACT

A light therapy system is made up of a pressure cuff system having a cuff that is positionable on or near a body part of a user and that can receive pressurized air to selectively pressurize and depressurize the cuff and a light emitting system having a supporting structure and a light emitter positioned on the supporting structure, the light emitter being controllably powerable. The supporting structure is positionable on an interior surface of the cuff so that the light emitter can direct light onto the body part. The light therapy system can further include a controller capable of controllably powering the light emitter, wherein controller can adjust the intensity or duration of the light directed onto the body part in response to an input or measurement related to a condition of the body part. A photometer can be provided separately or integrally to measure the condition of the body part. A method of providing light therapy is also provided.

20 Claims, 9 Drawing Sheets

(52) U.S. Cl.
CPC .............. *A61N 2005/0628* (2013.01); *A61N 2005/0652* (2013.01); *A61N 2005/0659* (2013.01)

(56) References Cited

U.S. PATENT DOCUMENTS

| | | | |
|---|---|---|---|
| 2007/0208395 A1* | 9/2007 | Leclerc | A61N 5/0616 607/86 |
| 2009/0082836 A1 | 3/2009 | Schell | |
| 2013/0030423 A1 | 1/2013 | Reichert et al. | |
| 2013/0085420 A1* | 4/2013 | Feinstein | A61N 1/0468 601/5 |
| 2016/0129279 A1† | 5/2016 | Ferolito | |
| 2017/0113063 A1* | 4/2017 | Geurts | A61N 5/0622 |
| 2017/0157431 A1* | 6/2017 | Cheatham, III | A61N 1/0476 |
| 2017/0304139 A1* | 10/2017 | Ross | A61H 11/00 |
| 2017/0319866 A1* | 11/2017 | Liu | A61H 39/04 |
| 2018/0015284 A1 | 1/2018 | Coleman et al. | |
| 2018/0193186 A1 | 7/2018 | Wright et al. | |
| 2018/0228689 A1* | 8/2018 | Lach | A61H 39/007 |
| 2018/0318600 A1 | 11/2018 | Tapper et al. | |
| 2020/0016031 A1* | 1/2020 | Hsien | A61H 39/04 |

\* cited by examiner
† cited by third party

LIGHT THERAPY SYSTEM

PRIORITY

The present application claims the benefit of domestic priority based on U.S. Provisional Patent Application 62/802,686 filed on Feb. 7, 2019, the entirety of which is incorporated herein by reference.

BACKGROUND

Photobiomodulation (PBM) or Low-level light therapy (LLLT) involves the application of laser and light-emitting diode (LED) light to living tissue to create a photobiostimulation effect. The application of laser and LED light to living tissue is performed using wavelengths between 600-1000 nm and power from 5-500 mW. Research has shown that the PBM accelerates wound healing, improves microcirculation, and improves muscle performance. In most studies, an infrared (IR) light source is placed on or near the surface of the body to produce a therapeutic dose of light at 0.5 to 5.0 J/cm2. Various light sources include commercially available LEDs and lasers diodes packaged in integrated circuits. Some laser-based devices are pulsed to deliver higher instantaneous radiation intensity without thermally damaging the treated tissue.

A biphasic dose response effect is well established in the PBM treatment, with which, any therapeutic benefits are diminished above and below some optimal dosage range. Thus, accurate PBM dosing of muscles is critical for achieving benefits but confounded by limited and variable penetration depth of the IR light that is applied on the skin surface for treating the tissues beneath the skin surface.

Inside the tissue, photons are either scattered or absorbed. The therapeutic benefit is achieved when light is absorbed by mitochondria in the muscle. On most parts of the body, a portion of the IR light passes through the skin, and the underlying fat layer scatters the photons in a random pattern. Some photons continue to the underlying muscle fibers where the IR energy is absorbed by chromophores. The beneficial effects of the IR radiation of the muscle tissue increases mitochondrial membrane potential, oxygen consumption, and adenosine triphosphate (ATP) production. Since the IR light passing through the fat is randomly scattered, delivering a precise dose of the IR fluence to the body muscles is challenging given humans have varying levels of skin melanin and fat layer thickness throughout their bodies.

Near IR photometry is used in some commercial products (such as Lipid meter, SAT meter, FUTREX) to non-invasively measure skin fat thickness. The method uses light that is transmitted into the skin by IR emitting diodes. This radiation penetrates the tissue and is reflected, absorbed, and scattered according to the tissue's optical properties. The radiation emerging from the skin is detected at multiple distances between the source and detector of the optical measuring system and then processed to infer the amount of light absorbed by the skin and reflected back from the fat layer.

Intermittent pneumatic compression (IPC) devices are used medically to help prevent blood clots in the deep veins of the legs (deep vein thrombosis). These devices use pneumatic cuffs that are usually placed around the legs. The cuffs fill with air and squeeze the legs. Upon release of the air, blood flows back through the veins and helps prevent blood clots. Recently, these devices have been used by athletes to improve circulation and facilitate muscle recovery after exercise. Also, the IPC devices are commercially available and frequently marketed to provide automated massage treatment. The IPC devices come in a variety of forms to treat different parts of the body and muscle groups. Leg units cover the foot and leg to the upper thigh. Shorts begin above the knee and extend upward above the waist. Some cuffs cover hands and arm up to the shoulder.

Therefore, there is a need for an improved light therapy system. There is a further need for a light therapy system with improved and/or more consistent dosing. There is a further need for a light therapy system with improved delivery of light to the muscles. There is a further need for improved and/or coordinated determination of fat layer thickness. There is a further need for a light therapy system that is used in conjunction with an intermittent pneumatic compression device.

SUMMARY

The present invention satisfies these needs. In one aspect of the invention, an improved light therapy system and improved method of providing therapeutic light is provided.

In another aspect of the invention, a light therapy system and method of use provides improved dosing and/or more consistent dosing.

In another aspect of the invention, a light therapy system and method of use provides improved delivery of light therapy to the muscles of a user.

In another aspect of the invention, a light therapy system and method of use utilizes fat layer thickness information for improved light therapy.

In another aspect of the invention, a light therapy system and method of use utilizes skin color information for improved light therapy.

In another aspect of the invention, an improved fat layer thickness determination and method is provided.

In another aspect of the invention, a light therapy system and method of use is used in conjunction with an intermittent pneumatic compression device.

In another aspect of the invention, a light therapy system comprises a pressure cuff system comprising a cuff that is positionable on or near a body part of a user and that can receive pressurized air to selectively pressurize and depressurize the cuff; and a light emitting system comprising a supporting structure and a light emitter positioned on the supporting structure, the light emitter being controllably powerable; wherein the supporting structure is positionable on an interior surface of the cuff so that the light emitter can direct light onto the body part, and wherein the light emitter has a light emitting surface, the light emitting surface being a sufficient height from the supporting structure that the light emitting surface can be pressed into the skin and into a fatty layer of the body part when the cuff is pressurized.

In another aspect of the invention, a light therapy system comprises a pressure cuff system comprising a cuff that is positionable on or near a body part of a user and that can receive pressurized air to selectively pressurize and depressurize the cuff; and a light emitting system comprising a supporting structure and a light emitter positioned on the supporting structure, the light emitter being controllably powerable; wherein the supporting structure is positionable on an interior surface of the cuff so that the light emitter can direct light onto the body part, and wherein the light emitter has a light emitting surface, the light emitting surface being a sufficient height from the supporting structure that the light emitting surface can be pressed into the skin and into a fatty layer of the body part when the cuff is pressurized, wherein the light emitter comprises a plurality of arrays of light emitters, each associated with a different muscle group of the body part.

In another aspect of the invention, a light therapy system comprises a pressure cuff system comprising a cuff that is positionable on or near a body part of a user and that can receive pressurized air to selectively pressurize and depressurize the cuff; and a light emitting system comprising a supporting structure and a light emitter positioned on the supporting structure, the light emitter being controllably powerable; wherein the supporting structure is positionable on an interior surface of the cuff so that the light emitter can direct light onto the body part, and wherein the light emitter has a light emitting surface, the light emitting surface being a sufficient height from the supporting structure that the light emitting surface can be pressed into the skin and into a fatty layer of the body part when the cuff is pressurized and further comprising a photometer capable of measuring a property of the body part.

In another aspect of the invention, a light therapy system comprises a pressure cuff system comprising a cuff that can is positionable on or near a body part of a user and that can receive pressurized air to selectively pressurize and depressurize the cuff; a light emitting member comprising a supporting structure and a light emitter positioned on the supporting structure, wherein the supporting structure is positionable on an interior surface of the cuff so that the light emitter can direct light onto the body part; and a controller capable of controllably powering the light emitter, wherein controller can adjust the intensity or duration of the light directed onto the body part in response to an input or measurement related to a condition of the body part.

In another aspect of the invention, a light therapy system comprises a pressure cuff system comprising a cuff that can is positionable on or near a body part of a user and that can receive pressurized air to selectively pressurize and depressurize the cuff; a light emitting member comprising a supporting structure and a light emitter positioned on the supporting structure, wherein the supporting structure is positionable on an interior surface of the cuff so that the light emitter can direct light onto the body part; and a controller capable of controllably powering the light emitter, wherein controller can adjust the intensity or duration of the light directed onto the body part in response to an input or measurement related to a condition of the body part, wherein the controller adjusts the intensity or duration of the light in response to a thickness of the fat layer of the body part.

In another aspect of the invention, a light therapy system comprises a pressure cuff system comprising a cuff that can is positionable on or near a body part of a user and that can receive pressurized air to selectively pressurize and depressurize the cuff; a light emitting member comprising a supporting structure and a light emitter positioned on the supporting structure, wherein the supporting structure is positionable on an interior surface of the cuff so that the light emitter can direct light onto the body part; and a controller capable of controllably powering the light emitter, wherein controller can adjust the intensity or duration of the light directed onto the body part in response to an input or measurement related to a condition of the body part and further comprising a photometer and wherein the controller adjusts the intensity or duration of the light in response to a signal from the photometer.

In another aspect of the invention, a light therapy system comprises a pressure cuff system comprising a cuff that can is positionable on or near a body part of a user and that can receive pressurized air to selectively pressurize and depressurize the cuff; a light emitting member comprising a supporting structure and a light emitter positioned on the supporting structure, wherein the supporting structure is positionable on an interior surface of the cuff so that the light emitter can direct light onto the body part; and a controller capable of controllably powering the light emitter, wherein controller can adjust the intensity or duration of the light directed onto the body part in response to an input or measurement related to a condition of the body part, further comprising a plurality of photometers and wherein the controller adjusts the intensity or duration of the light in response to a signal from the photometers, wherein the photometer generates a signal in relation to the thickness of the fat layer of the body part or the transmissivity of the body part, wherein the light emitter comprises a plurality of arrays of light emitters, each associated with a different muscle group of the body part, and wherein each photometer is positionable on the interior surface of the cuff in proximity to a respective array.

In another aspect of the invention, a method of providing light therapy comprises providing a pressure cuff having a light emitter on an interior surface thereof; positioning the cuff on or near a body part; inflating the cuff and pressing the light emitter directly or indirectly against the skin of the body part; determining the intensity or duration of light to be applied from the light emitter to the body part in relation to a condition of the body part; and powering the light emitter so that the light is applied to the body part at the determined intensity or duration.

In another aspect of the invention, a method of providing light therapy comprises providing a pressure cuff having a light emitter on an interior surface thereof; positioning the cuff on or near a body part; inflating the cuff and pressing the light emitter directly or indirectly against the skin of the body part; determining the intensity or duration of light to be applied from the light emitter to the body part in relation to a condition of the body part; and powering the light emitter so that the light is applied to the body part at the determined intensity or duration, further using a photometer to measure the condition of the body part and using the measurement to determine the intensity or duration of the light.

In another aspect of the invention, a light therapy system comprises a photometer having concentric rings of photometer light emitters and a central photodetector.

In another aspect of the invention, a method of providing light therapy comprises providing a photometer; using the photometer to determine a condition of a body part; and applying light therapy to the body part at an intensity or duration related to the condition of the body part.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to a light therapy system. In particular, the invention relates to a light therapy system including or utilizable with a pressure cuff. Although the invention is illustrated and described in the context of being useful in association with intermittent pneumatic compression, the present invention can be used in other ways, as would be readily apparent to those of ordinary skill in the art. Accordingly, the present invention should not be limited just to the examples and embodiments described herein.

Figure 1A:
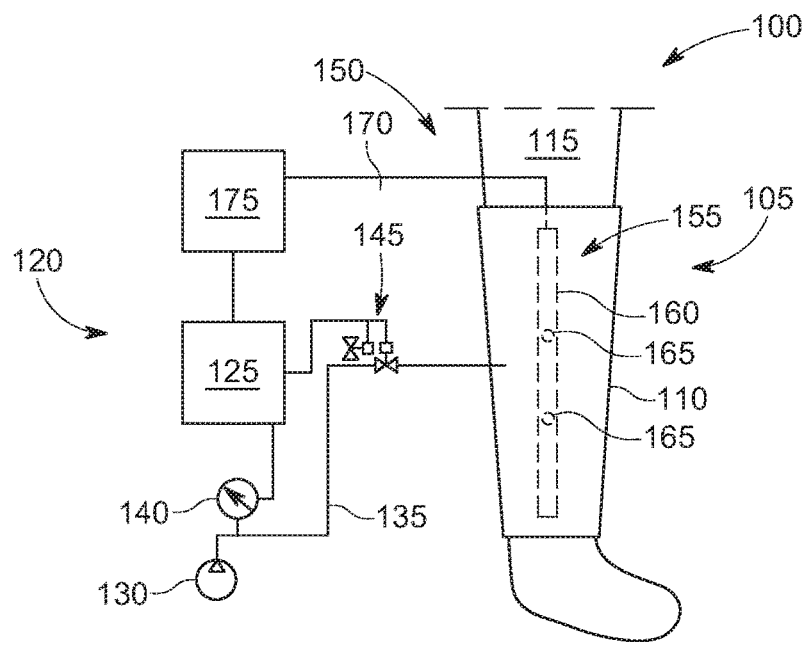
FIG. 1A is a schematic side view of a light therapy system according to the invention.

FIG. 1A shows a light therapy system 100 of the present invention. The light therapy system 100 includes or can be useable with a pressure cuff system 105. The pressure cuff system 105 includes a pressurizable cuff 110 that can be received around, adjacent, or in proximity to at least a portion of a part of a body, such as an extremity. In FIG. 1A, the cuff 110 is shown encircling a leg 115 of a user. The pressure cuff system 105 also includes a control system 120 that controls and/or monitors the pressurization of the cuff 110. The control system 120 includes a pressure controller 125 that is capable of controlling the operation of an air pump 130, such as an electrical air pump or a source of pressurize air, so that pressurized air may be passed through a line 135 leading to the cuff 110 to inflate or pressurize the cuff 110. The pressure controller 130 can receive information from a pressure sensor 140 and can control the application of pressure to the cuff 110 in response to the received pressure data. The pressure controller 130 may also be capable of controlling a pressure gate 145 within the line 135. The pressure gate 145 can include solenoids and/or venting mechanisms to allow the cuff 110 to be selectively pressurized and depressurized.

The light therapy system 100 also includes a light emitting system 150 positionable within the cuff 110 of the pressure cuff system 105 so that light can be administered to the portion of the leg 115 or other body part within the cuff 110. The light emitting system 150 includes one or more light emitting members 155 that include a supporting structure 160 that supports one or more light emitters 165. The light emitting system 150 is controllably connected, such as by electrical wire 170 and/or wireless technology, to a light emitting controller 175 of the control system 120. The light emitting controller 175 is capable of controlling and/or monitoring the application of light, including the dose or dosage of light applied to the leg 115 or other body part. By dose or dosage of light applied it is meant the intensity and/or duration of the light application. Optionally, the light emitting controller 175 can be incorporated into or in communication with the pressure controller 125 so that the application of pressure and the application of light can be responsive to one another and/or coordinated together. The supporting structure 160 can take the form of a printed circuit board or the like through which each light emitter 165 can be powered and/or controlled.

Figure 1B:
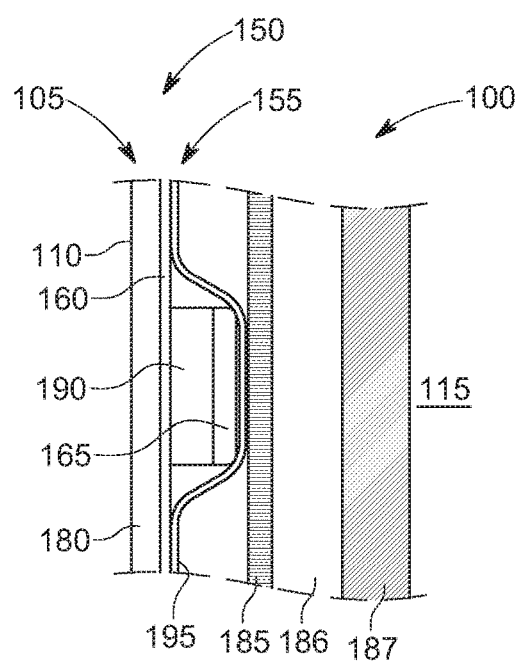
FIG. 1B is a schematic sectional view of the light therapy system of FIG. 1A in an unpressurized condition.
Figure 1C:
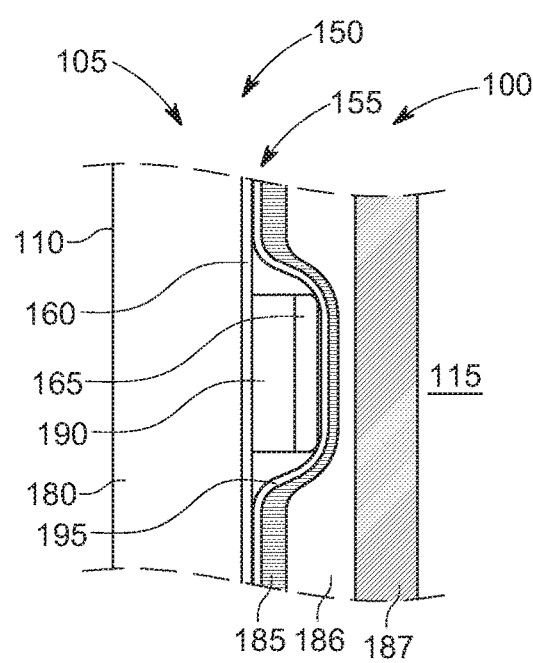
FIG. 1C is a schematic sectional view of the light therapy system of FIG. 1A in a pressurized condition.

FIGS. 1B and 1C show a sectional view of the light emitting system 150 positioned within the cuff 110 of the pressure cuff system 105 so that a light emitter 165 can be in proximity to the leg 115 or other body part and can deliver light to the body part. For example, the light emitting member 155 or the light emitters 165 can be positioned on the inside or on an interior surface of the cuff 110. The cuff 110 is made of a flexible material and includes a hollow space 180 that is in communication with the line 135 of pressurized air. The hollow space 180 may be selectively pressurized and depressurized to inflate and deflate the cuff 110. FIG. 1B shows the cuff in an unpressurized condition, and FIG. 1C shows the cuff in a pressurized condition. As can be seen, in the unpressurized condition, the light emitter 165 rests near or against the skin 185 of the leg 115 or other body part without significant deformation of the skin 185. However, when in the pressurized condition shown in FIG. 1C, the pressure of the cuff 110 forces the light emitter 165 into the skin 185. When sufficient pressure is applied, the light emitter 165 can be further pressed into the fatty layer 186 so that it is in proximity to the muscle 187. Optionally, a spacer 190 or the like can be provided if needed to increase the thickness of the light emitter 165 and to extend the distance of the light emitter from the supporting structure 160. Also optionally, a cover layer 195 made of light transmitting material can be provided to cover the light emitter 165 so that it does not directly contact the skin 185. Alternatively, the cover layer 195 can be removed and the light emitter can directly contact the skin 185.

In one version, the light therapy system 100 may be used to administer therapeutic light to the leg 115 or other body part that is within or near the cuff 115. For example, the light therapy system 100 may be used to administer photobiomodulation therapy, also known as low-level light therapy, where the application of laser or light emitting diode (LED) light to living tissue. Therapeutic light that is administered to create a photobiostimulation effect when administered using wavelength of light between about 600 and 1000 nm at a power ranging from about 5 to 500 mW from each light source. The photobiostimulation effect has been shown to accelerate wound healing, improve circulation, and/or improve muscle performance. The light therapy system 100 of the present invention improves on previous attempts at light therapy by its inclusion within the pressure cuff system 105 which applies pressure to the light emitting system 150 to press the light emitter 165 into the skin 185 and closer to the muscle 187 or other target of therapy. By positioning the light emitter 165 closer to the muscle, a greater therapeutic effect can be achieved and/or greater efficiency is light application can be achieved. When light is applied to the surface of the skin 185, photons are either scattered or absorbed. The scattering is especially prevalent in the fatty tissue 186. The positioning of the light emitter 165 closer to the muscle 187 and the compression of the fatty layer 186 allows for increased absorption of the photons by the muscle and decreased scattering. The therapeutic effect is achieved when photons are absorbed by mitochondria in the muscle. The beneficial effect of the photon absorption is believed to include an increase in mitochondrial membrane potential, oxygen consumption, and adenosine triphosphate production.

In one version of the light therapy system, the one or more light emitters 165 comprises one or more light emitting diodes. In one particular version, the light emitters 165 are configured to emit light consisting of wavelengths in the near infrared range or from about 780 nm to about 1000 nm. While it is possible to use light outside this range, studies have shown that light in this range of wavelengths is preferred for muscle therapy since shorter wavelengths do not penetrate as far into tissue and longer wavelengths are not as effective at stimulating the muscle mitochondria.

In one version of the light therapy system 100, the light emitters 165 are sized and shaped to penetrate into the fatty layer 186 when the cuff 110 is pressurized so that the light emitter can be in proximity to the underlying muscle 187. The light emitters 165 have a light emitting surface that is in contact with the skin 185 either directly or through the cover layer 195. In one version, the height of the light emitting surface above, i.e. away from, the support structure or an interior surface of the cuff 110 is at least about 1 mm, or at least about 2 mm, or at least about 3 mm, or at least about 5 mm, or at least about 10 mm. A spacer 190 can be provided as necessary or the light emitter 165 can be designed with the desired height. In one version, different height light emitters can be provided to accommodate different fat layer thickness of a user.

Figure 2A:
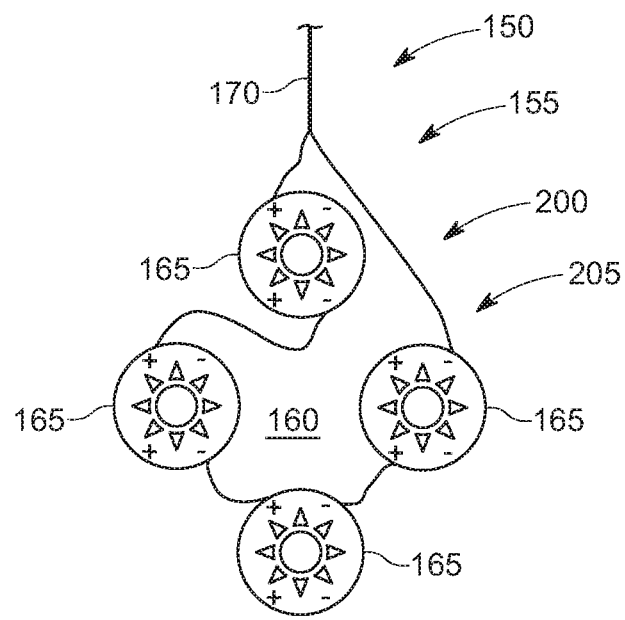
FIG. 2A is a schematic top view of a version of a light emitter array of the light therapy system.
Figure 2B:
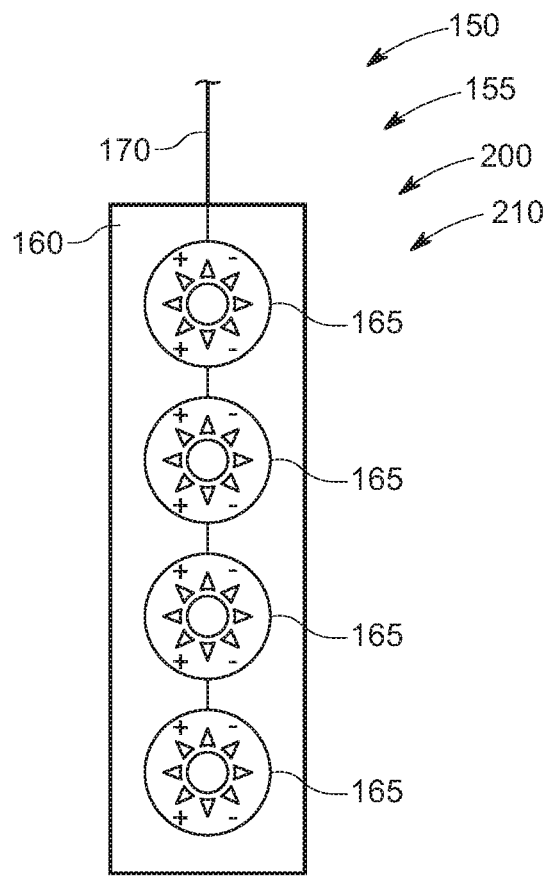
FIG. 2B is a schematic top view of another version of a light emitter array of the light therapy system.

FIGS. 2A and 2B illustrate versions of light emitting members 155 that are designed to provide an array 200 of light emitters 165. The array 200 can comprise a plurality of light emitters 165 arranged in any suitable pattern. By array of light emitters it is meant a group of a plurality of light emitters 165 that are powerable with by the light emitter controller at the same or similar intensity and duration. The array 200 can be on one printed circuit board or can be on multiple printed circuit boards, and a single printed circuit board can contain one or multiple arrays 200. For example, the array 200 of FIG. 2A is a multidimensional array 205, and the array 200 of FIG. 2B is a one-dimensional array 210 or strip of light emitters 165 positioned generally in a straight line. The light emitting system 150 can comprise one or more such arrays 200. For example, in one version, the array 200 can encompass the entirety or near entirety of the interior of the cuff 110. In another version, one or more arrays 200 can be positioned within the cuff 110 so that they each apply light to a particular region or muscle of interest on the body part within the cuff 110. For example, in one particular version, one or more arrays 200 of light emitters 165 can be attached to the cuff 110 in independently controlled groups that correspond to target leg muscle groups such as quadriceps, hamstrings, and/or calves. Alternatively or additionally, other muscle groups or other tissue can be targeted. In one version, the one or more arrays 200 are individually integrated circuits mounted to flexible printed circuit boards that are attachable the cuff 110. In one version, one or more arrays 200 are connected in series to a main two connector power wire that is connected to the light emitting controller 175.

The light emitting controller 175 controls the operation of the one or more arrays 200 of light emitters in a predetermined manner. The light emitting controller 175 supplies power to the one or more light emitters 165 so that a predetermined intensity and/or duration of light can be administered to a body part near or contacting the light emitter. The power and/or duration can be applied to a single light emitter 165 or to a plurality of light emitters 165. When a plurality of light emitters 165 are to be powered by the light emitting controller 175, they may be powered independently or as one or more arrays 200 where each array 200 includes a group of light emitters 165 that are to be powered collectively as a group at the same or similar intensity and for the same or similar duration. The intensity and/or the duration of the application of light for each light emitter 165 and/or for each array 200 can be input into the controller by a user communicating with the controller via a user interface. Alternatively, the intensity and/or duration can be automated. For example, in one version, the light emitting controller can be in communication with the pressure controller 125 or other monitor and can adjust the application of light in response to the pressurization of the cuff 110. For example, by applying light to the body part only when the cuff 110 is pressurized, the application of light can be more efficient since it is during this pressurized condition that the light more optimally is transmitted to the muscle 187. Alternatively, the light can be maintained even when the cuff 110 is in an unpressurized condition. Also alternatively or additionally, the intensity and/or duration can be adjusted in response to other signals or conditions as discussed below.

In one version, the intensity and/or duration of the application of light by a light emitter 165 and/or one or more arrays 200 of light emitters 165 can be selected or adjusted based on a factor associated with the body part to the treated. For example, one factor that can be used to adjust the intensity and/or duration of the light application is the thickness of the fatty layer 186 of the body part. Because the scattering of light is especially prevalent in fatty tissue, the thicker the layer of fat 186, the higher the scattering of light and the greater the needed intensity and/or duration of light application to achieve a desired light application dosage. Accordingly, in one version, the thickness of the fatty layer 186 of the body part can be measured, such as by calipers or by an electronic monitor, and the intensity and/or duration of the light application can be set depending on the measurement. An operator of the light therapy system 100 can, for example, input the desired intensity and/or duration into the light emitting controller 175 after referring to a chart, table, or the like, that has empirical data relative to the fat layer condition, or the light emitting controller can be preprogrammed with the empirical data so that the operator can input the measurement information and the light emitting controller 175 can automatically adjust the intensity and/or duration of the light application. Alternatively, when using an electronic monitor, a signal related to the fat level condition can be supplied to the light emitting controller 175 and the adjustments can be made in response to the signal. Another factor that can be used to adjust the intensity and/or duration of the light application is skin color. Skin color can affect the transmissivity of the light application. Therefore, in one version of the invention, skin color can be assessed or monitored, and the light intensity and/or duration can be adjusted in accordance with the skin color in similar manner to that described above in connection with the fat condition.

In yet another version, both fat layer thickness and skin color can be used to adjust the intensity and/or duration of the light intensity.

Figure 3A:
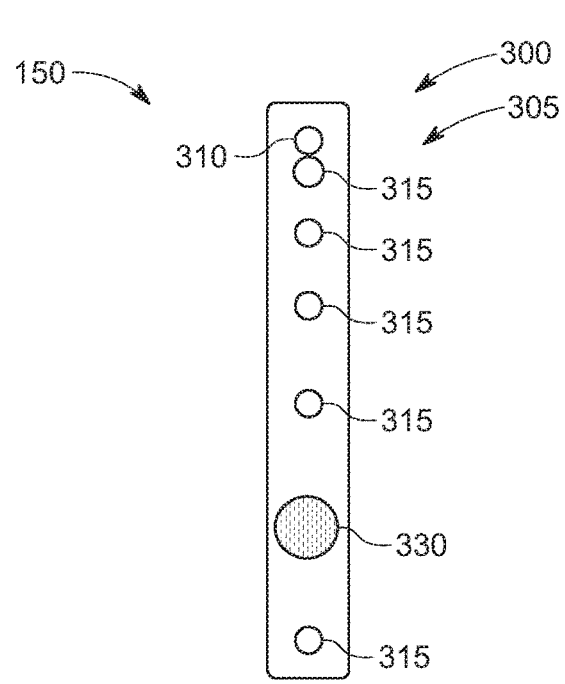
FIG. 3A is a schematic top view of a monitoring system of the light therapy system.
Figure 3B:
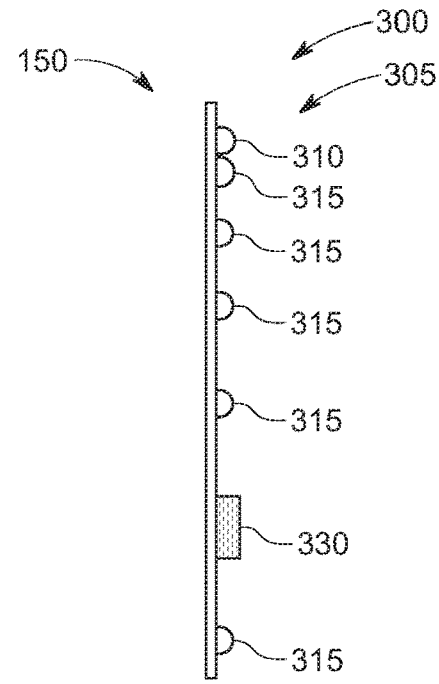
FIG. 3B is a schematic side view of the monitoring system of FIG. 3A.

In one version, the light therapy system 100 may also include a light sensing system 300, such as the one shown in FIGS. 3A and 3B. In the version of FIGS. 3A and 3B, the light sensing system comprises a photometer 305, such as a reflectometer. The photometer 305 is made up of a photodetector 310 and a plurality of photometer light emitters 315, such as infrared light emitting diodes. The photodetector 310 and the photometer light emitters 315 are secured to a substrate 320. The photometer 305 comprises the photodetector 310 and a pattern of the photometer light emitters 315 that are spaced at logarithmic distances away from the photodetector 310. For example, the photometer light emitters 315 may be infrared light emitting diodes that are placed at 3 mm, 6 mm, 12 mm, 24 mm, and/or 48 mm distances from the photodetector 310. The photodetector 310 may include an optical filter on the sensor to detect only light within a narrow wavelength around the peak emitted wavelength of the infrared light emitting diodes 315. In one, such as the one shown in FIGS. 3A and 3B, five photometer light emitters 315 and the photodetector 310 are mounted on a rigid substrate 320, as shown, so that their relative spacing is maintained when the cuff 110 is inflated. Photometer light emitter power lines and sensor wires may be bundled together so the photometer 305 is in communication with the light emitting controller 175. The light emitting controller 175 can control the emission of light from the photometer light emitters 315 and can receive an output signal from the photodetector 310. The light emitting controller 175 can then process the data to determine qualities related to the transmission of light into the leg 115 or other body part. An optional pressure sensor 330 may also be provided as discussed below.

In use of the photometer 305 of FIGS. 3A and 3B, infrared photons from the photometer light emitters 315 are applied to the skin 185. The photons are scattered, absorbed, or reemitted at the skin surface. The skin 185 has both light scattering and absorbing properties. The absorption is greater on darker skin with an abundance of melanin. Fat 186 may be approximated at mostly scattering of the infrared light. Muscle 187 tissue is primarily absorbing. The attenuation of light at the shortest distance between a first photometer light emitter 325 or group of photometer light emitters and the photodetector 310 is highly correlated with the skin light absorption since typical skin thicknesses on the torso and limbs is similar to 3 mm distance between the first photometer light emitter 325 and the photodetector 310. The skin light absorption may be obtained from the empirical relationship:

$$\text{skin absorption (cm}^{-1}) = f(\text{photodetector voltage from first light emitter})$$

Light that penetrates the skin layer is scattered in all directions by the fat layer 186. Some of this light exits the body back through the skin 185 and may be detected by the photodetector 310. Light that passes through the fat layer 186 is absorbed by the muscle 187 where it can provide the desired therapeutic effect. Over thick fat layers, the amount of light remitted at the skin 185 will be higher than over thin fat layers 186 where light can travel less obstructed to the muscle tissue 187. Each photometer light emitter is turned on and off in sequence so the output voltage from the photodetector 310 at different times corresponds to the diffuse reflectance at a discrete distance on the skin surface. The fat layer 186 thickness is inferred from the multiple measurements of the photometer light emitters 315 at varying distances from the photodetector 310. The fat layer 186 thickness may be calculated from the empirical relationship:

$$\text{fat thickness (mm)} = g(\text{photodetector voltage from all light emitters})$$

Figure 3C:
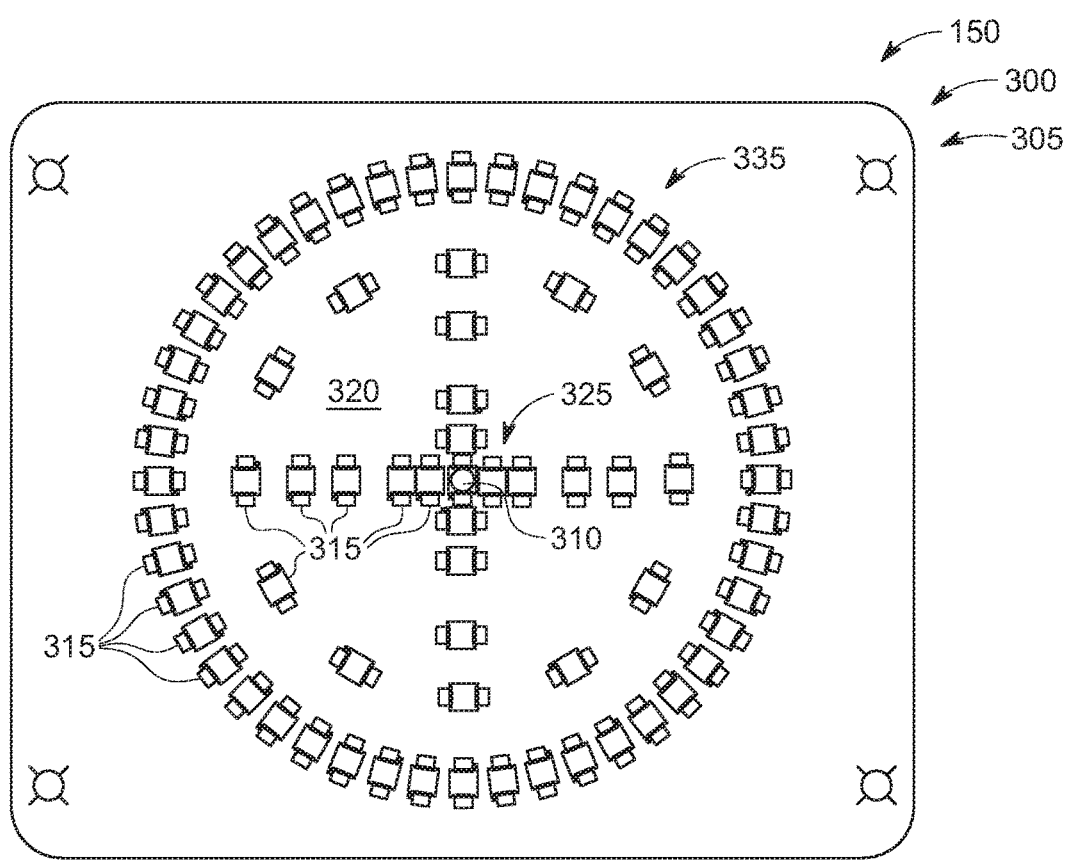
FIG. 3C is a schematic top view of another version of a monitoring system of the light therapy system.

Another version of a photometer 305 of the light sensing system 300 of the light therapy system 100 is shown in FIG. 3C. The photometer 305 of FIG. 3C includes a circular geometric pattern 335 of photometer light emitters 315 with the photodetector 310 in the middle of the circular pattern surrounded by strings of one or more photometer light emitters 315. Each string corresponds to a unique distance between the string and the photodetector 310 and is independently controllable by the light emitting controller 175. The current through each string of photometer light emitters 315 is modulated to provide a response at the photodetector 310 that is approximately consistent for a typical skin color and fat thickness. The photodetector voltage response may be near the middle of the range for an analog to digital converter to accurately measure the diffuse reflectance with a 10+bit resolution.

In one version, the light sensing system 300 can be used independently from the light application. For example, prior to the installation of the cuff 110 on the body part, the light sensing system 300 can be used to make measurements of the body part, such as the fat layer thickness and/or the light transmissivity. The measurements can be delivered to, input into, and used to set the light emitting controller 175, as discussed above.

In one version, the light sensing system 300 can be integrated into the cuff 110 by being positioned within the cuff 110 and be directly connectable to the light emitting controller 175. In this version, the photometer 305 can be used to make measurements of the body part prior to the application of light to the body part so the intensity and/or duration of the application can be adjusted. Additionally or alternatively, the photometer 305 can be used during the application of light. In one particular version, the photometer 305 can be used to monitor the transmissivity of light during the application, and the measurement can be interpreted by the light emitting controller 175 so that automated adjustments can be made to the intensity and/or duration of the light application. One or more photometers 305 can be positioned within the cuff 110 at a position in proximity to the one or more arrays 200 of light emitters 165 so that the intensity and/or duration of the light application for each array 200 can be separately adjusted in response to the measurement from the photometer associated with the region where the array 200 is located. The adjustments to the intensity and/or duration can be made by an operator receiving a signal indicative of the measurements or can be automatically made by light emitting controller 175 in response to the signal from the photometer 305. In one version, the adjustments are made by the light emitting controller 175 in real time. For example, in one version, a photometer 305 may be positioned or mounted near the center of each of the one or more arrays 200 of light emitters 165.

In one version, such as shown in FIG. 1 and in 4, the light therapy system 100 may include a pressure cuff system 105 that operates as an intermittent pneumatic compression (IPC) device 400. Intermittent pneumatic compression devices are used medically to help prevent clots in deep veins in the legs or other extremities. The intermittent pneumatic compression device 400 intermittently applies pneumatic pressure to the leg or other extremity or body part. Upon release of pressure, blood flows back through the veins and helps prevent blood clots. Intermittent pneumatic compression devices can also or alternatively be used by athletes to improve circulation and facilitate muscle recovery after exercise and/or for automated message treatment.

Figure 4:
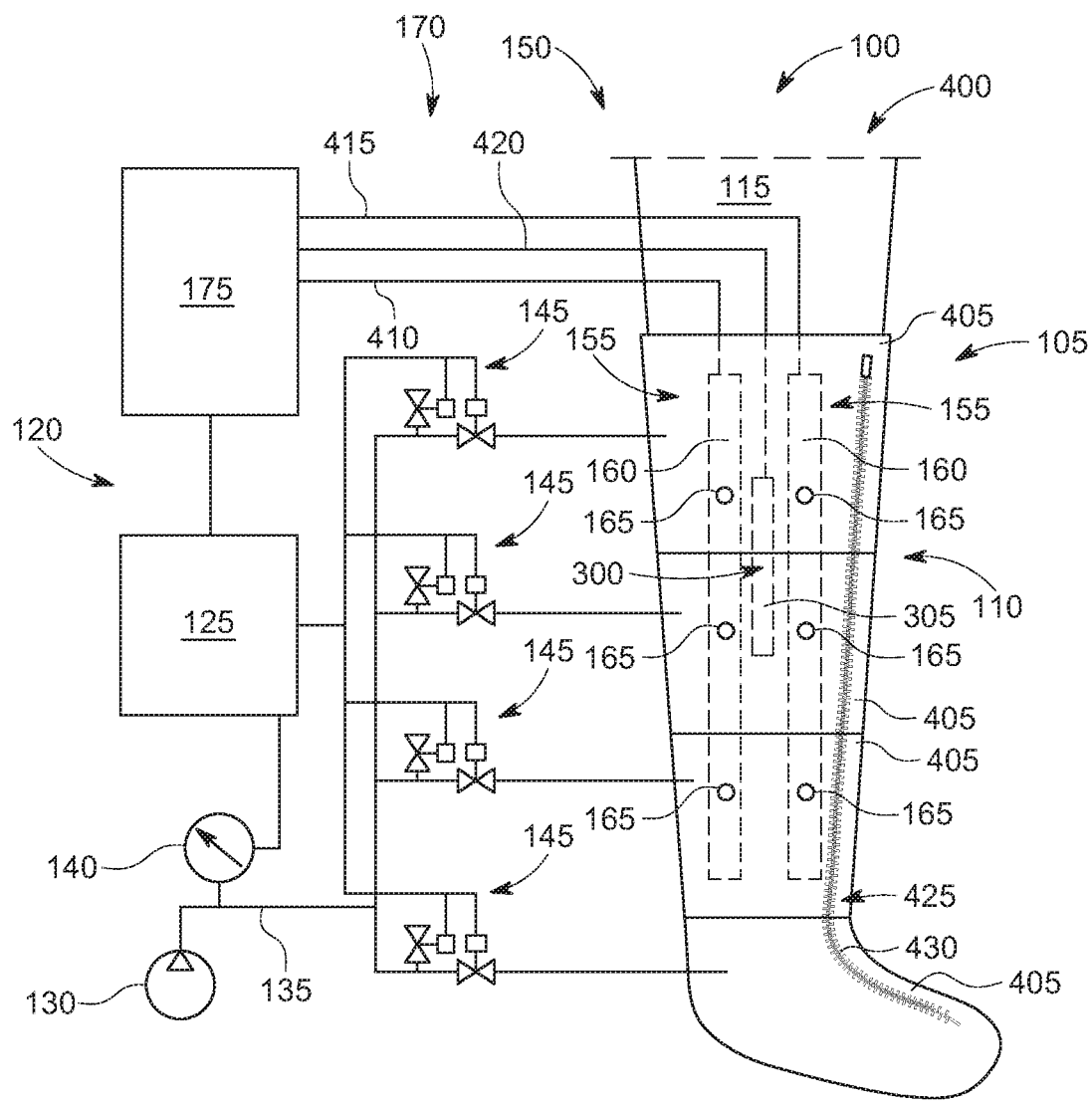
FIG. 4 is a schematic side view of another version of a light therapy system of the invention.

In the version of FIG. 4, the pressure cuff system 105 includes a cuff 110 having multiple chambers 405 that are each pneumatically separated from one another. When being used as an intermittent pneumatic compression device 400, the pressure controller 125 can separately pressurize and depressurize each separate chamber 405 for a desired effect, such as to sequentially pressurize the chambers 405 in series to help encourage the flow of blood. In another version, the pressure controller 125 can pressurize each chamber 405 at the same time but with each chamber 405 being pressurized a different amount, as desired.

In FIG. 4, there is further shown an exemplary light emitting system 150 having two or more light emitting members 155 that span multiple compartments 405 and a light sensing system 300 comprising a photometer 305 positioned between the light emitting members 155. In an alternative arrangement, each light emitting member 155 can be associated with a separate compartment 405 and separate photometers 305 can be provided for multiple light emitting members 155. The light emitting controller 175 is in electrical communication with each light emitting member 155 by, for example, respective wires 410, 415 and is in communication with the one or more photometers 305, such as by bundled wire 420 that can both power the photometer light emitters 315 and receive an output signal from the photodetector 310. The light emitting controller 175 may include a processor and/or circuitry that controls the light emitting members 155 and may include input devices such as a touchscreen for receiving operator input. The light emitter power supply voltage and the air pump 130 may be connected to a mains power supply or a rechargeable battery for drawing electrical power, and provides the electrical power to the light emitters 165 as desired. The light emitting members 155 may be arranged in electrical series groups so that the sum of forward voltages of the group's light emitters 165 match the power supply voltage. The input device, such as the touch screen, may be utilized by a user to set a desired muscle infrared dose, for example.

The cuff 110 of the light therapy system 100 may optionally include a side opening 425. The side opening 425 may be selectively openable to expose the interior of the cuff 110 and to facilitate attachment of the cuff 110 onto a leg or other extremity or other body part. A closure 430, such as a zipper or the like, may be provided to close the opening 425 once the cuff 110 is secured around the body part.

Figure 5:
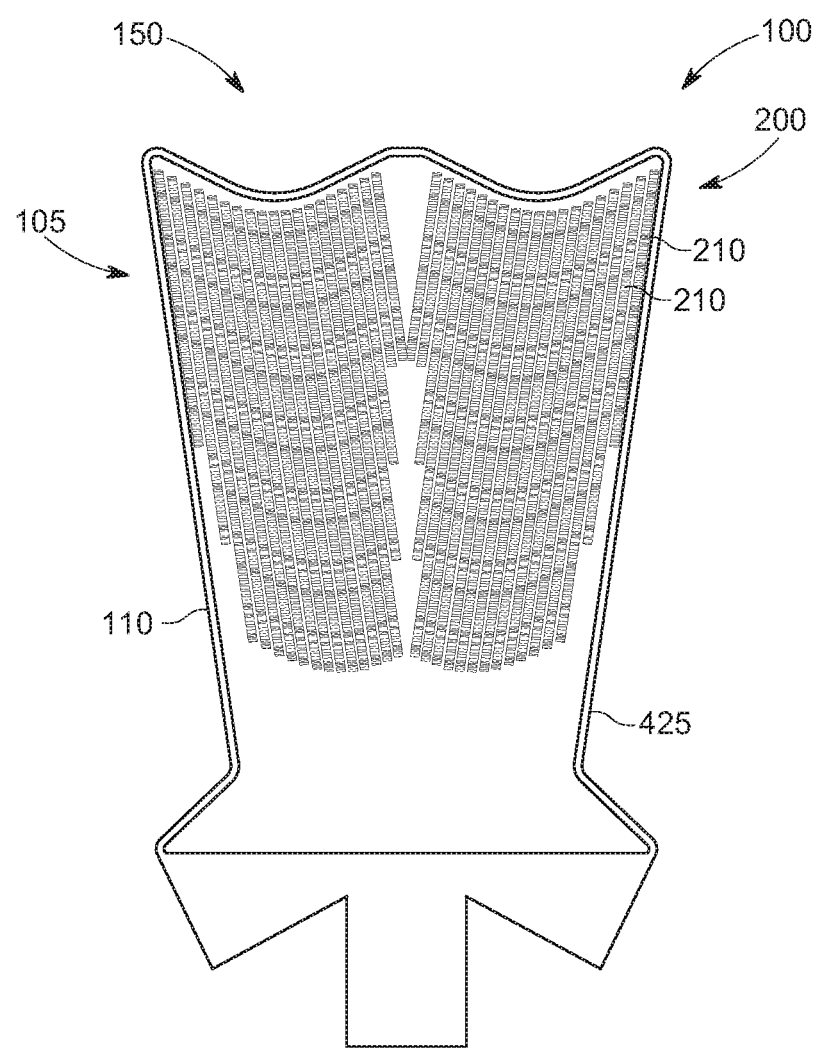
FIG. 5 is a schematic open view of a version of an arrangement of light emitters of the light therapy system.

FIG. 5 shows a particular cuff 110 and light emitting system 150. The light emitting system 150 of FIG. 5 includes multiple strips of light emitters 165, such as strips of light emitting diodes. In this version, each strip can operate as an array 200 or as a one-dimensional array 210 of light emitters 165. Alternatively, multiple strips can be grouped together to form a larger array 200 or a multidimensional array. Alternatively, the entirety of the strips can collectively form a single array 200. Each one-dimensional array 210 can contain from 2 to 100 light emitters 165. In one version, there can be from 2 strips to about 50 strips, or from about 10 strips to about 40 strips, or from about 20 strips to about 30 strips, or about 26 strips. The total number of light emitters 165 can range from 2 to about 20,000, or from about 50 to about 10,000, or about 1000 to about 5000, and in one particular version there are about 4800 light emitters. The photometers 305 can optionally be mounted near the center of an array 200 of independently controllable light emitters 165. The total number of photometers 305 can range from 0 to 20, or from about 1 to about 5, and in one particular version, there are four photometers 305, one each for the right and left side of the calf and for the right and left side of the quadricep.

Figure 6:
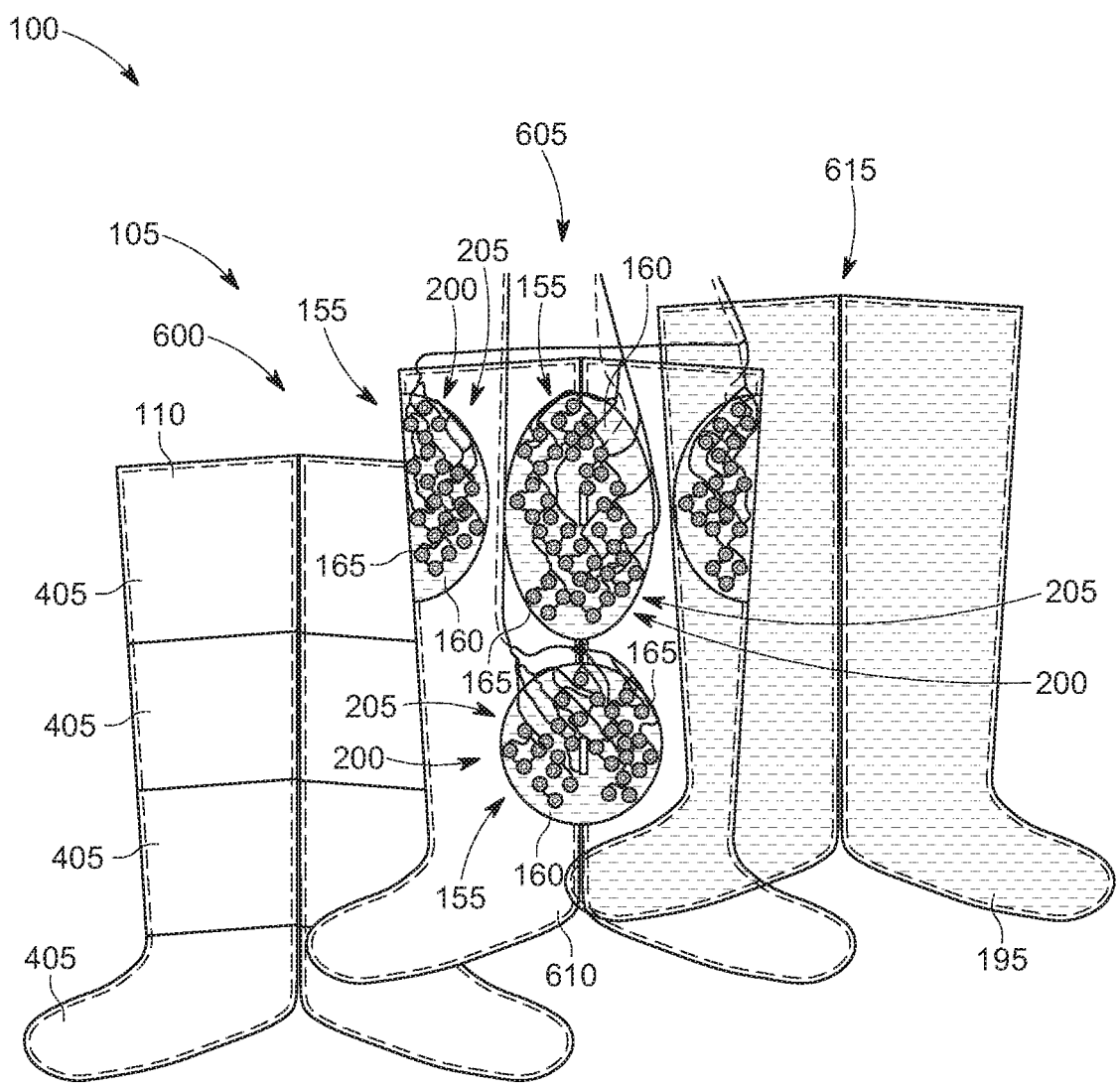
FIG. 6 is a schematic exploded view of a version of a pressure cuff system of the light therapy system.

FIG. 6 shows an exploded view of a version of a pressure cuff system 105 of the light therapy system 100 with the cuff open and laid flat. The pressure cuff system 105 includes a cuff 110 that serves as an outer layer 600. An intermediate layer 605 includes the one or more light emitting members 155 and the supporting structures 160 and the light sensing system 300. Optionally, the intermediate layer 605 can further include a reflective liner 610, such as a white liner. The reflective liner 610 can be attached to the cuff 110 and can be cut to be the same size and shape as the cuff 110 or can be different size and shape. The attachment of the reflective liner 610 to the cuff 110 may be in the form of zippers, hook and loop fasteners, or snap tape around the edges of the cuff 110 and/or each cuff chamber 405 or each cuff chamber that allow for convenient removal and servicing. The intermediate layer 605 may use zippers or other fasteners that mate with commercially available cuffs. Each side of the intermediate layer 605 may have two fasteners, one to attach to the cuff 110 and another to close the cuff 110 and intermediate layer 605 around a body part. The reflective or white liner 610 can improve the uniformity of the light dosage reaching the muscles. The light that is scattered back through the skin may be reflected back into the body by the reflective liner 610 to increase the chance of photons reaching the muscle tissue more efficiently. An inner layer 615 may also be provided. The inner layer 615 may be made of a material that is optically transparent to infrared light, such as polyvinyl chloride, polyurethane, epoxy, acrylic, silicone, and the like, and is attached to the intermediate layer 605 as a sheet with a fastener material or may be permanently attached thereto. The purpose of the optically transparent inner layer 615 is to insulate the user from the electrical components and provide a cleanable surface that can be disinfected and wiped down between uses. The permanently attached version of the inner layer 615 can be adhered to the intermediate later 605 to create a durable product that provides protection for the light emitters 165 and photometers 305 from abrasion and the like. In this version, the inner layer 615 makes up the optional cover layer 195 discussed above. The light emitting members 155 may be arranged in the electrical series groups so that the sum of forward voltages of the group's light emitters match the light emitter power supply voltage. The one or more series groups are connected to the main two connector power wire that is ultimately connected to the light emitting controller 175 that may be separated from the intermediate layer 605. In one version, the light emitter members 155 may contain infrared light emitting diodes mounted to heat dissipating aluminum printed circuit boards that are attached to the white liner 610 using removable fastener or permanent attachment.

In one version, the intermediate layer 605 and optionally the inner layer 610 can be provided as an upgrade kit for an existing intermittent pneumatical compression device cuff assembly. Alternatively, the pressure cuff system 105 can include the cuff 110 and additional layers constructed together as a single unit.

In one version of the light therapy system 100, a photometer 305 may be mounted near the middle of each muscle group array 200 so the dose delivered by the light emitters 165 on the array 200 may be controlled and/or customized in accordance with the signal received from the photometer 305, as shown in FIG. 6. Alternatively, multiple photometers 305 can be associated with each array 200, such as by being distributed around the periphery or at respective ends of the array 200. Alternatively, a single photometer 305 can be provided at a desired location.

Figure 7:
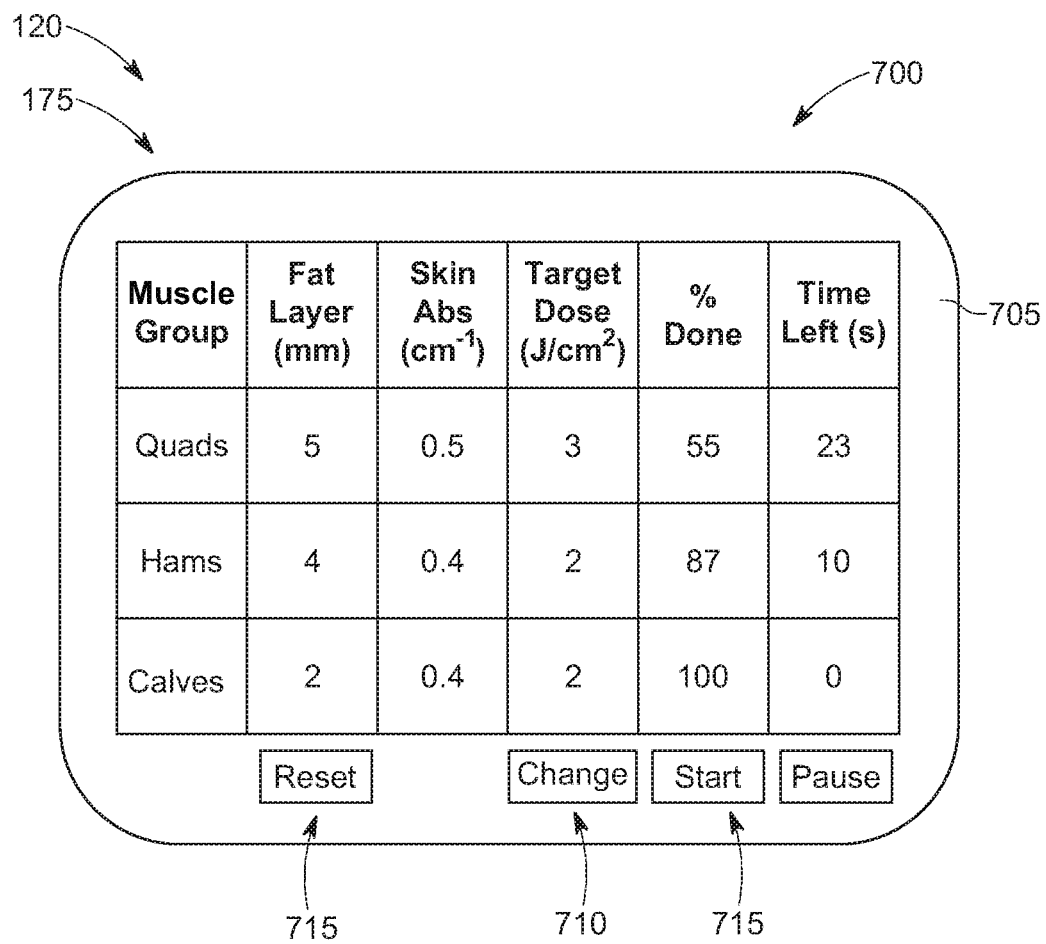
FIG. 7 is a schematic representation of a display of a controller of the light therapy system.

FIG. 7 illustrates an example of a user interface 700, such as a touch screen 705, that may be used to allow a user to interact with the control system 120 and in particular the light emitting controller 175. The user interface 700 shows parameters and status of infrared dosing for the light therapy system 100 applied to a leg 115. The user interface 700, for example, can be utilized by the user to specify the desired muscle IR dose (in joules per cm2) for each muscle group by using of a change tab or button 710. In real time, a display of the touch screen 705 user interface 700 may indicate one or more parameter values corresponding to fat thickness, skin light absorption, target muscle dose, progress toward the delivered muscle dose for each muscle group, and time remaining to complete the dosage. The touch screen 705 may further facilitate or allow or include a mechanism that will allow the user to reset the delivered dose counter and start and pause the ongoing dosing by way of other tabs or buttons 715.

Figure 8A:
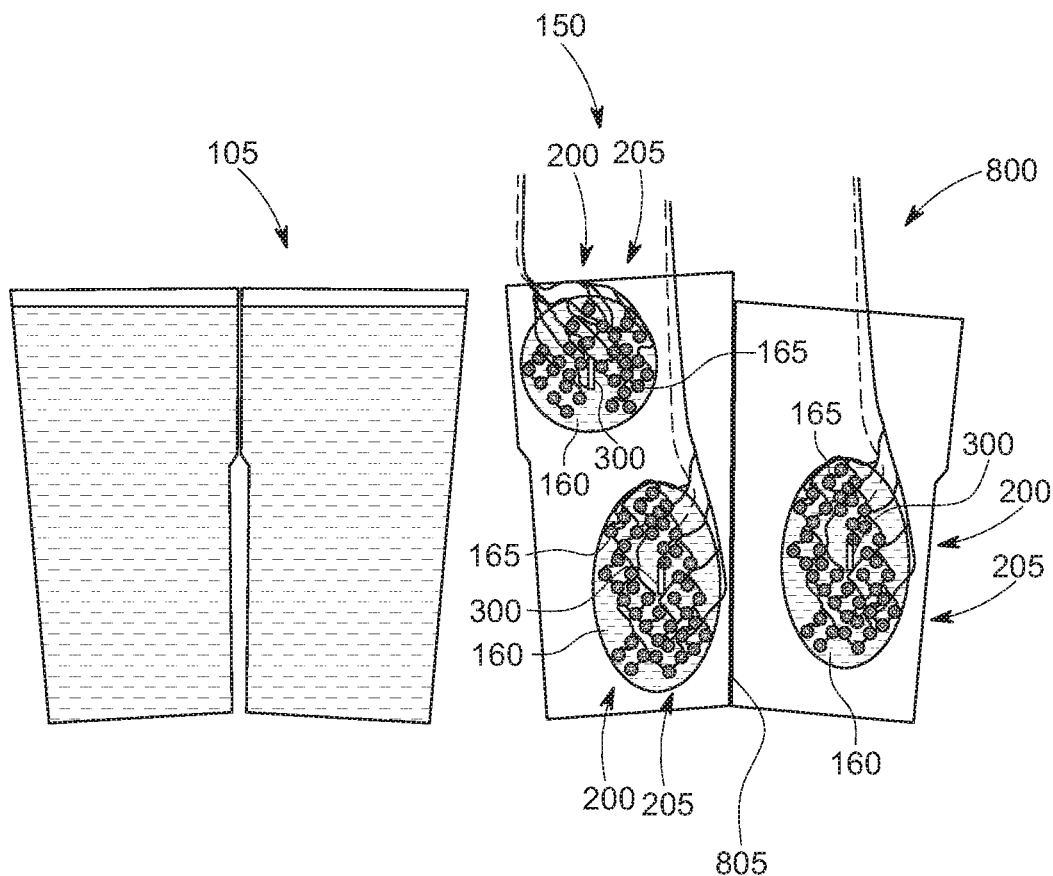
FIG. 8A is a schematic exploded view of another version of a pressure cuff system of the light therapy system.
Figure 8B:
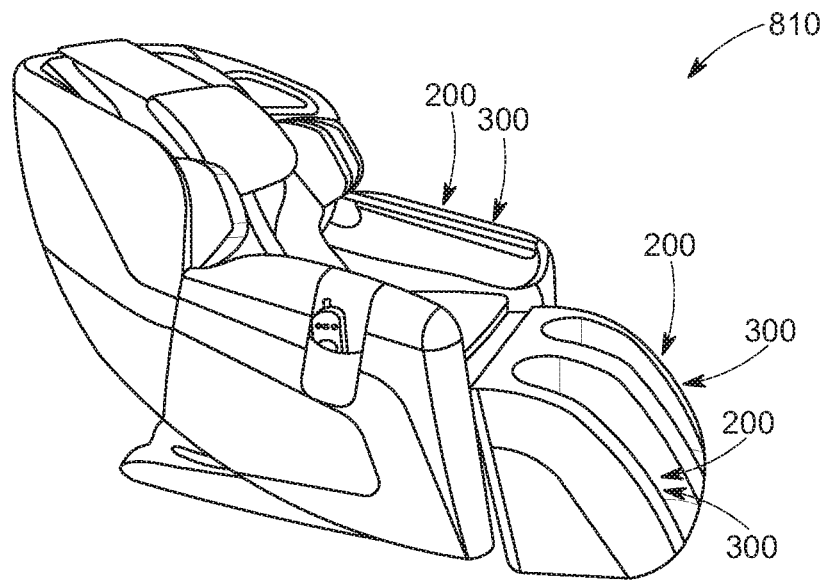
FIG. 8B is a schematic exploded view of another version of a pressure cuff system of the light therapy system.

FIGS. 8A and 8B show different versions of pressure cuff systems 105 of the light therapy system 100. FIG. 8A shows the pressure cuff system 105 in the form of intermittent pneumatic compression shorts 800 that cover large muscle groups in upper legs and buttocks. In this version, the muscle group arrays 200 are applied in compression shorts 800 that cover the midsection of the body. When the middle seam 805 of the shorts 800 are opened and laid flat, the muscle group arrays 200 are applied in regions that correspond with the gluteus maximus, hamstrings, and quadriceps. FIG. 8B shows a version of the pressure cuff system 105 integrated into or positionable on a massage chair 810 where the muscle group arrays 200 and light sensing systems 300 are integrated into installed on the chair 810 to treat muscle groups in arms, legs, neck, and/or back of a human body. In one version, the muscle group arrays 200 may be mounted in the massage chair so that the user receives the therapeutic light dose when the massage elements are creating maximum pressure on the targeted muscle groups. Commercially available massage chairs treat neck, shoulder, back, buttocks, arm, thigh, and calf muscles. The muscle group arrays 200 and light sensing systems 300 may be installed in a plurality of these locations as a kit where the array and sensors interface with the massage chair controls. Alternatively, the light therapy system 100 may be directly incorporated in the design of a massage chair. Alternatively, the light therapy system 100 may be an integral part of other structures, such as a massage table, or the like.

In operation, the light therapy system 100, in one version, can employ a variety of programs that inflate the pressure cuff system 105 in a desired manner. Target cuff pressures are achieved either by inflating the cuff 110 and/or compartments 405 in the cuff 110 for a specific period of time or by monitoring the line pressures connected to the cuff 110. When the maximum cuff pressure is achieved, a first solenoid valve or the like, such as a solenoid from one of the pressure gates 145 connecting a pump, such as the electrical air pump 130 to the cuff 110 may close or the pump may stop. A second solenoid valve or the like, such as another solenoid from the pressure gate 130, may vent the cuff 110 or compartment 405 to release the pressure according to a program schedule. The photometer 305 light emitting controller 175 may connect to the pressure controller 125 to monitor and control voltages corresponding to the state of the solenoid valves, the pressure sensor 140, and the pump motor. Based on these control signals, a processor within the light emitting controller 175 determines a state when the cuff 110 or each compartment 405 is at a maximum pressure. The photometer 305 and the array 200 of light emitters 165 may operate when they are located underneath the cuff 110 that is at a desired and/or predetermined pressure state. When the solenoid vents the air in the cuff 110 or compartment 405, both the photometer 305 and the arrays 200 may be disabled. A typical session with an intermittent pneumatic compression system may last approximately 15 minutes. The pump may go through multiple cycles that may last a few minutes each where the cuff 110 or compartments 405 are inflated to the certain pressure and the pressure is held for 5 to 30 seconds before venting the cuff 110 or compartment 405. The light emitting controller 175 may, in one version, wait until a first predetermined pressure event occurs and make readings from the photometer 305 to characterize the light absorption and scattering of the skin and fat layers. These measurements may be used to calculate a dose of the IR light on the surface of the skin that will provide a uniform dose of the IR light to the muscles that will be absorbed in the muscle layer. The skin dose (DS) may have the form as shown below:

$$DS=DT*h(\text{skin absorption, fat thickness})$$

Where DT, dosage time, is the cumulative period when the light emitters are activated.

While the cuff 110 or compartment 405 is still in the pressurized condition, the array 200 of light emitters 165 may activate to begin the infrared light dose. The processor of the light emitting controller 175 may log the number of seconds for which the array 200 of light emitters are turned ON. The light emitters 165 may then be turned OFF when the corresponding cuff solenoid vents and turns back ON when the cycle reaches the predetermined pressure and/or duration. When the timer reaches the calculated exposure time for the target dose of the array 200, the lights may turn OFF for the remainder of the program schedule.

In operation, each array 200 of light emitters 165 includes a number of light emitters 165 that emit light in a range of wavelengths spanning a central wavelength. The radiant flux (mW) of each light emitter is a measure of the emitted light in the range of wavelengths through an active area on the chip. The light emitter radiant power density is the radiant flux divided by the active area (mW/cm$^2$). The light emitter radiant power density applies only to a point where the active area of the light emitter is in contact with the skin. For each array 200 and for each associated muscle group, a surface radiant power density is calculated. The surface radiant power density may be calculated as the number of light emitters 165 in the group multiplied by the radiant flux of an individual light emitters divided by the area treated by the group or array 200. Beneath the skin and fat layers, the muscle radiant power density is the measure of how much of the light reaches the underlying muscle. The spacing of the light emitters on the array 200 of the muscle group light assembly can be important for proper therapeutic light dosing since too few lights may create dark regions between lights where the light does not propagate through to the muscle layer. Each array 200 has the light emitters spaced to deliver a nearly homogeneous power density to the target muscle. The ensemble of the light emitters may have sufficient radiant power to deliver the dose within the allotted time where the intermittent pneumatic compression program has the underlying cuff in the predetermined pressure state.

For areas of the body with thicker fat layers, less radiant power reaches the muscle group. The light reaching the muscle is also more diffuse. More powerful light emitters 165 may be spaced further apart but still achieve the desired homogeneity and density of light at the muscle layer. For example, a typical thickness of fat on a male calf (gastrocnemius muscle) is 4 mm+/−2 mm whereas the fat thickness on the inner thigh (adductor muscle) is 10 mm+/−4 mm. To deliver a homogeneous 3 J/cm² dose of the infrared radiation to both muscle groups in a 30 s exposure time, the inter light emitter spacing over the calf muscle group assembly may need to be 2 cm and use 200 mW radiant power light emitters and the light emitter spacing over the adductor may be 5 cm and use 1000 mW light emitters.

In another version, specific focusing and/or diffusing lenses may be placed over the light emitters 165 to help ensure uniform light density on the muscle surface. With this version, the array 200 of muscle group light emitters may be customized for different fat layer thickness without changing the light emitter spacing. The array 200 of muscle group light emitter assemblies could then be moved to target different muscle groups for a variety of intermittent pneumatic compression cuff assemblies, for example hand, foot, arm, legs, hips, thighs, and/or waist. In another version, a pressure sensor 330 is mounted on each photometer 305. The array 200 may be turned ON when a pressure above a threshold value is sensed above the associated muscle group. The dosing may continue while the pressure is above the threshold value and the total exposure time is less than that needed to achieve the desired muscle dose. In another version, the light emitting controller 175 uses pulse width modulation (PWM) to control the dosage of light. The light emitting controller 175 may determine a duty cycle of the light emitters 165 associated with each muscle group so that the dosage of all muscle groups is completed at the same time.

Figure 9A:
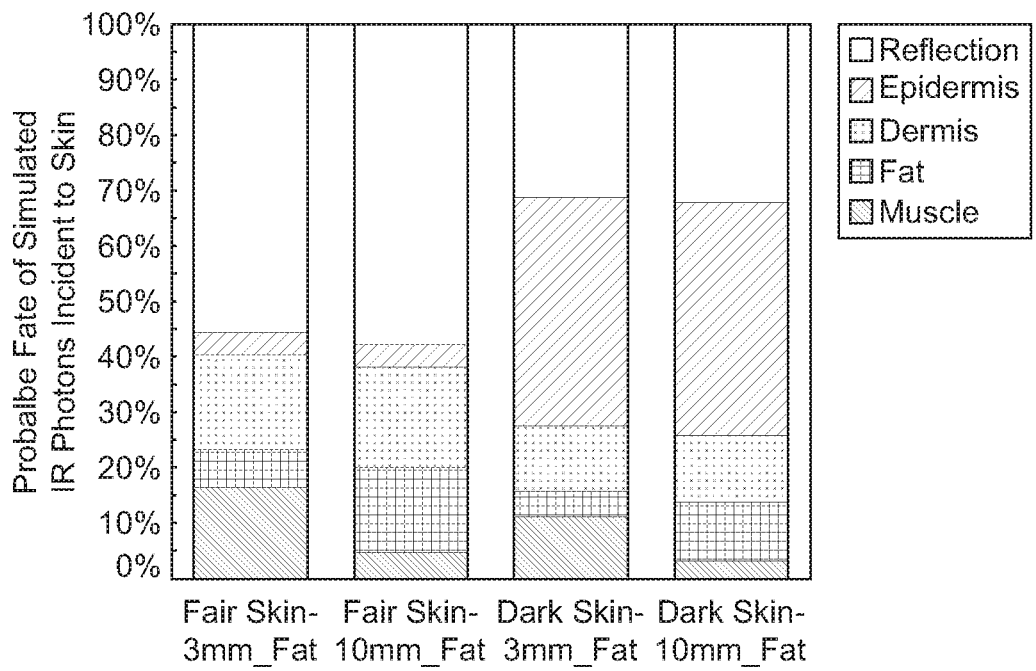
FIG. 9A is a chart showing fate of infrared photons for multiple simulations changing both melanin content ranging from fair to dark skin color and fat thickness from 3 mm to 10 mm.

Modeling of light transport through multiple tissue layers is a complex problem that can be addressed with statistical simulations that model the transport and fate of a large number of photons entering the body normal to the skin surface and interacting with the various tissue layers. The inputs of Monte Carlo simulations include optical properties of each tissue layer and their corresponding thicknesses. The output is a map of where photons are absorbed in tissue or re-emitted out of the skin. A summary of the modeled fate of IR photons for multiple simulations (changing both melanin content ranging from fair to dark skin color and fat thickness from 3 mm to 10 mm) is shown in FIG. 9A. In this simulation, the amount of light absorbed in the muscle layer ranges from 17% for fair skin and 3 mm fat layer to 3.2% for dark skin and 10 mm fat layer. To achieve the same dose of IR light to the underlying muscle, the later subject would need to expose themselves to more than 5 times the amount of light than the former subject. Inferring how much light reaches the muscle is helpful for delivering a consistent dose.

Figure 9B:
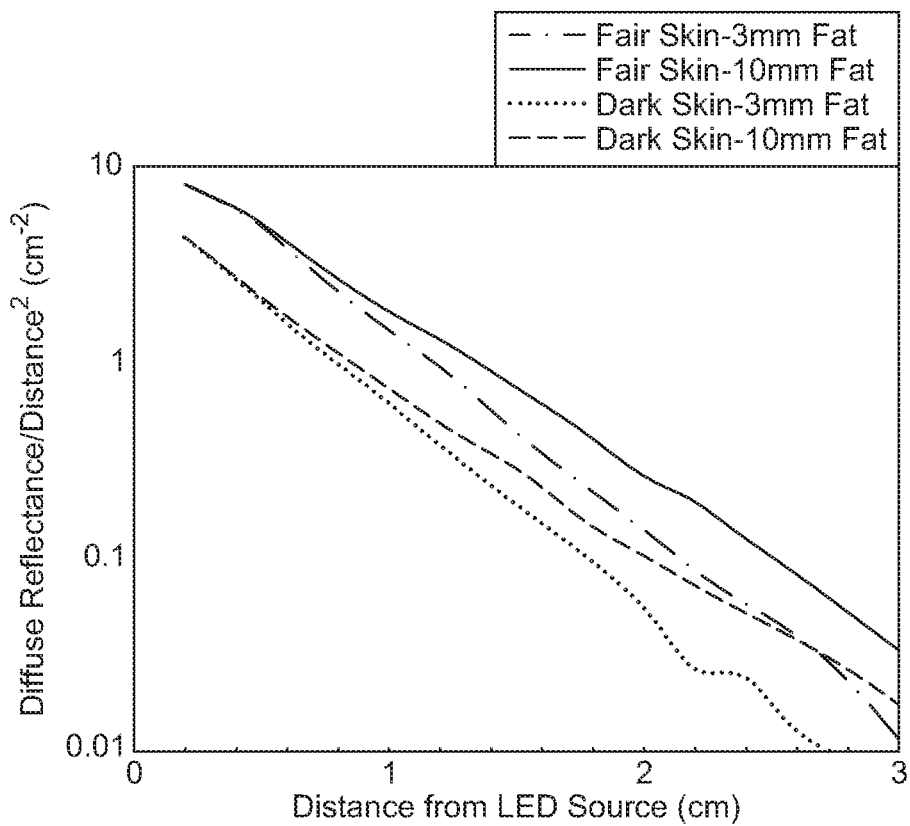
FIG. 9B is a graph showing a profile of how light is re-emitted from the skin surface as a function of distance from a light emitter light source.

The model also generates a profile of how light is re-emitted from the skin surface as a function of distance from the light emitter light source, FIG. 9B. For points very close to the light emitting source (x<4 mm, point A in FIG. 9B), the diffuse reflectance, $R_d(A)$=detector signal/distance², is closely related to how much light is not absorbed by the melanin in the epidermis layer. At source-detector distances on the order of the dermis thickness, the fat and muscle layers below the dermis have negligible effect on the $R_d(A)$ signal. The skin factor, $F_{skin}$ may be defined as $R_d(4$ mm$)$ and represents a characteristic of the diffuse reflectance curve.

Light that penetrates the skin layer is scattered in all directions by the fat layer.

Some of this light exits the body back through the skin and may be detected by the photodetector 310. Light that passes directly through the fat layer is absorbed by the muscle where it can provide the desired effects of the light therapy. Over thick fat layers, the amount of light reemitted at the skin will be higher than over thin fat layers where light can travel with less obstruction from the photometer light emitters 315 to the light absorbing muscle tissue. The output voltage from the photodetector 310 at different times corresponds to the diffuse reflectance across a range of distances on the skin surface. The fat layer thickness is inferred from the multiple measurements light emitted from the skin 185 and varying distance from the source. Experiments have shown that further from the light emitter 315 source (>5 mm), $R_d(x)$ decays exponentially where the rate of decay is related to the thickness of the fat layer. The fat factor may be simply defined as the ratio $R_d(10$ mm$)/R_d(20$ mm$)$ cancels out the component of the signal that is related to skin absorption.

For each model simulation, the skin and fat factors are tabulated and a collection of model runs with a range of different skin color and fat thickness layers creates a database for inferring the fraction of light absorbed by the muscle tissue, as shown by the following table of a sample database to infer infrared treatment time to deliver a constant dose of infrared light to muscle tissue based on variations in skin color and fat layer thickness.

|  | Fair Skin-3 mm Fat | Fair Skin-10 mm Fat | Dark Skin-3 mm Fat | Dark Skin-10 mm Fat |
| --- | --- | --- | --- | --- |
| Fitzgerald Skin Color Type | 1 | 1 | 5 | 5 |
| Fat Layer Thickness (mm) | 3 | 10 | 3 | 10 |
| Skin Factor, Rd(4 mm) | 36.7 | 37.6 | 16.6 | 16.9 |
| Fat Factor, Rd(10 mm)/Rd(20 mm) | 43.0 | 28.2 | 43.5 | 28.9 |
| Abs_muscle | 17% | 5% | 11% | 3% |
| Treatment Time (min) | 10.0 | 35.3 | 14.7 | 51.2 |

Direct measurements of the reflectometer at distances of 4 mm, 10 mm, and 20 mm enable the calculation of both the skin and fat factors. In turn, the measured factors can be matched and interpolated with data from the above table to determine the proper treatment time that will deliver a constant dose of infrared light to muscle tissues for most users.

In other versions, the light therapy system 100 may use other parameters derived from the skin reflectometer's diffuse reflectance profile to infer adjustments to dosing treatment times. In addition, other data such as photometer sensor pressure 330 may be added to the database to improve the precision of infrared light dosing.

The power supply for the components and controllers may be integrated into a single enclosure and the light source is activated when the IPC pump has reached the predetermined pressure in the cuff 110. In this way, the light is only emitted when the optical path from the light source module to the muscle is shortest. The controller can be set with a prescribed total infrared or other radiation dosage (J or J/cm2) for each muscle group so that the muscle group light source is turned OFF when the desired dosage has been achieved.

In one version of the invention, the light sensing system 300 can be used with a light therapy system other than one that uses a pressure cuff system. Light therapy of all types can benefit from a measurement of the thickness of a fatty layer and the adjustment of the light dosage in relation to the measurement. For example, the light sensing system 300 can be used to determine optimal light dosage on the skin to deliver the desired light dosage to the muscle tissue in any other mode of infrared light therapy. Other light therapy systems include light bulbs (Wolezek) and LED panels (i.e. Joovv, PlatimunLED Therapy Lights) where a subject stands in front of the light for a predetermined period of time. Other methods can also include tanning bed style systems (NovoThor). In addition, hand-held LED and laser IR emitters (Infarex, TOPlight) can be held on the skin surface to achieve therapeutic effects. Optical properties of skin color and fat thickness from clinical test subjects may be approximated and used as input to the multi layered Monte Carlo model. The model will determine what fraction of IR photons incident to the subject's skin are absorbed in the muscle tissue. Using the relationships between diffuse reflectance profile from the IR photometer output and the faction of light absorbed in the muscle layer (Abs_muscle) from Table 1, an adjustment to the Treatment Time or light intensity can be calculated that will deliver a dose of IR light to the muscle tissue.

The control system 120 including the pressure controller 125 and/or the light emitting controller 175 can be any device capable of receiving input, performing calculations, performing calculations based on the input, producing an output signal, and/or producing an output signal as a result of the calculations. The controllers 125, 175 may be part of the same controller or may be separate controllers that are capable of communication with one another. The controllers 125, 175 may be in the form of a central processor that is capable of interacting with a user via a keyboard, a graphical user interface, wireless communication, voice command, or any other manner. For example, the controllers 125, 175 may be a personal computer, a laptop, a handheld device, a server, a network of servers, a cloud network, or the like. The operator may interact with the controller 125 and/or controller 175 before, during, or after the light therapy procedure. The controllers 125, 175 can include various modules that allow it to perform calculations, algorithms, routines, and/or subroutines to process information and/or make determinations. The controllers 125, 175 may further include other optional modules, such as artificial intelligence and/or machine learning modules that use algorithms to parse data, learn from the data, and then to make determinations and/or predictions based on what was learned.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Throughout this specification and any claims appended hereto, unless the context makes it clear otherwise, the term "comprise" and its variations such as "comprises" and "comprising" should be understood to imply the inclusion of a stated element, limitation, or step but not the exclusion of any other elements, limitations, or steps. Therefore, any appended claims should not be limited to the description of the preferred versions contained herein and should include all such alterations, permutations, and equivalents as fall within the true spirit and scope of the present invention.

What is claimed is:

1. A light therapy system comprising:
    a pressure cuff system comprising a cuff that is positionable on or near a body part of a user and that is configured to receive pressurized air to selectively pressurize and depressurize the cuff;
    a light emitting system comprising a supporting structure, at least one light emitter, and at least one spacer positioned between the supporting structure and each of the at least one light emitter, such that each of the at least one spacer is aligned with one of the at least one light emitter, the at least one spacer not extending past an edge of the light emitter, the at least one light emitter being controllably powerable;
    a cover layer disposed over a side of the at least one light emitter opposite the at least one spacer and in contact with the supporting structure, the cover layer configured to prevent direct contact between the at least one light emitter and the skin of the body part of the user; and
    wherein the supporting structure is directly attached to an interior surface of the cuff such that the at least one light emitter is configured to direct light onto the body part, and wherein the at least one light emitter has a light emitting surface, the light emitting surface being a sufficient height from the supporting structure that the light emitting surface is configured to be pressed into the skin and into a fatty layer of the body part when the cuff is pressurized.

2. A light therapy system according to claim 1 wherein the height of the light emitting surface is at least 3 mm.

3. A light therapy system according to claim 1 wherein the light therapy system comprises a plurality of arrays of light emitters, each associated with a different muscle group of the body part.

4. A light therapy system according to claim 1 wherein the supporting structure and the at least one light emitter are on a liner, the liner being removably attachable to the interior surface of the cuff.

5. A light therapy system according to claim 1 further comprising a photometer capable of measuring a property of the body part.

6. A light therapy system according to claim 1 further comprising a photometer positionable on the interior surface of the cuff.

7. A light therapy system according to claim 1 wherein the cuff is an integrated part of a chair.

8. A light therapy system comprising:
    a pressure cuff system comprising a cuff that is positionable on or near a body part of a user and that is configured to receive pressurized air to selectively pressurize and depressurize the cuff;
    a light emitting member comprising a supporting structure, at least one light emitter, and at least one spacer positioned between the supporting structure and the at least one light emitter, such that each of the at least one spacer is aligned with one of the at least one light emitter, the at least one spacer not extending past an edge of the light emitter, wherein the supporting structure and each of the at least one spacer are configured to be directly attached to an interior surface of the cuff such that the at least one light emitter is configured to direct light onto the body part;

a cover layer disposed over a side of the at least one light emitter opposite the at least one spacer and in contact with the supporting structure, the cover layer configured to prevent direct contact between the at least one light emitter and the skin of the body part of the user; and a controller capable of controllably powering the at least one light emitter, wherein the controller is configured to adjust the intensity or duration of the light directed onto the body part in response to an input or measurement related to a condition of the body part.

9. A light therapy system according to claim 8 wherein the controller is configured to adjust the intensity or duration of the light in response to a thickness of a fat layer of the body part.

10. A light therapy system according to claim 8 wherein the controller is configured to adjust the intensity or duration of the light in response to a skin color of the body part.

11. A light therapy system according to claim 8 further comprising a photometer and wherein the controller is configured to adjust the intensity or duration of the light in response to a signal from the photometer.

12. A light therapy system according to claim 11 wherein the photometer is positionable on the interior surface of the cuff.

13. A light therapy system according to claim 11 wherein the photometer is configured to generate a signal in relation to a thickness of a fat layer of the body part or a transmissivity of the body part.

14. A light therapy system according to claim 8 wherein the light therapy system comprises a plurality of arrays of light emitters, each associated with a different muscle group of the body part.

15. A light therapy system according to claim 8 further comprising a plurality of photometers and wherein the controller is configured to adjust the intensity or duration of the light in response to a signal from the photometers, wherein the photometer generates a signal in relation to a thickness of a fat layer of the body part or a transmissivity of the body part, wherein the light therapy system comprises a plurality of arrays of light emitters, each associated with a different muscle group of the body part, and wherein each photometer is positionable on the interior surface of the cuff in proximity to a respective array.

16. A light therapy system according to claim 8 wherein the supporting structure and the at least one light emitter are on a liner, the liner being removably attachable to the interior surface of the cuff.

17. A method of providing light therapy, the method comprising:

providing a pressure cuff system comprising a cuff that is positionable on or near a body part of a user and that is configured to receive pressurized air to selectively pressurize and depressurize the cuff;

providing a light emitting system comprising a supporting structure, at least one light emitter, and at least one spacer positioned between the supporting structure and each of the at least one light emitter, such that each of the at least one spacer is aligned with one of the at least one light emitter, the at least one spacer not extending past an edge of the light emitter, the at least one light emitter being controllably powerable;

providing a cover layer disposed over a side of the at least one light emitter opposite the at least one spacer and in contact with the supporting structure, wherein the supporting structure is directly attached to an interior surface of the cuff such that the at least one light emitter is configured to direct light onto the body part, the cover layer configured to prevent direct contact between the at least one light emitter and the skin of the body part of the user;

positioning the cuff on or near the body part;

inflating the cuff and pressing the at least one light emitter indirectly against the skin of the body part;

determining the intensity or duration of light to be applied from the at least one light emitter to the body part in relation to a condition of the body part; and powering the at least one light emitter such that the light is applied to the body part at the determined intensity or duration.

18. A method according to claim 17 wherein the condition of the body part is the thickness of a fat layer of the body part or a skin color of the body part.

19. A method according to claim 17 further using a photometer to measure the condition of the body part and using the measurement to determine the intensity or duration of the light.

20. A method according to claim 19 wherein the photometer is positioned on the interior surface of the cuff.

* * * * *